United States Patent
Meloni et al.

(10) Patent No.: US 9,383,323 B2
(45) Date of Patent: Jul. 5, 2016

(54) WORKPIECE CHARACTERIZATION SYSTEM

(75) Inventors: Mark Anthony Meloni, The Colony, TX (US); John Douglas Corless, Dallas, TX (US); Andrew Weeks Kueny, Dallas, TX (US); Mike Whelan, Coppell, TX (US)

(73) Assignee: Verity Instruments, Inc., Carrollton, TX (US)

( * ) Notice: Subject to any disclaimer, the term of this patent is extended or adjusted under 35 U.S.C. 154(b) by 228 days.

(21) Appl. No.: 13/166,571

(22) Filed: Jun. 22, 2011

(65) Prior Publication Data

US 2012/0025097 A1 Feb. 2, 2012

(51) Int. Cl.
*G01N 21/64* (2006.01)
*G01N 21/896* (2006.01)

(52) U.S. Cl.
CPC ................. *G01N 21/896* (2013.01)

(58) Field of Classification Search
USPC ........................................ 250/458.1
See application file for complete search history.

(56) References Cited

U.S. PATENT DOCUMENTS 6,042,785 A * 3/2000 Harju .............................. 422/52

* cited by examiner

*Primary Examiner* — David Porta
*Assistant Examiner* — Hugh H Maupin

(57) ABSTRACT

A workpiece characterization system for obtaining simultaneous measurement of layer and photoluminescence properties of a workpiece. The workpiece characterization system includes an excitation light and an illumination light each impinging upon a surface of a workpiece whereby the workpiece emits photoluminescent light and encodes light from said illumination source with layer information. The excitation light and the illumination light are generated from a single light source. The light from the single light source is filtered to remove wavelengths of light that correlate to light wavelengths emitted from the workpiece as a result of excitation. Wavelengths that correlate to light reflected from the workpiece that may contain encoded information are not filtered.

20 Claims, 14 Drawing Sheets

WORKPIECE CHARACTERIZATION SYSTEM

BACKGROUND OF THE INVENTION

The present invention relates generally to workpiece characterization systems and methods of use. More particularly, the present invention relates to a system, method and software program product for exciting production light emitting diodes with a wide spectrum excitation light source capable of exciting a light emitting diode without interfering with photoluminescence emission light emitted there from.

Workpiece characterization systems are employed in a variety of industries, such as the semiconductor processing industry, for real-time and/or near-real-time monitoring of workpiece properties, modification and process control. Workpiece characterization systems may be integrated with a semiconductor processing tool and utilized in-situ for real-time process control or may be used in-line for feedback/feedforward control.

Due to the rapid advancement of the use of light emitting diodes ("LEDs") as energy efficient and "green" lighting technologies, characterization and yield control/analysis for LEDs has seen intense demand as market forces drive product reliability up and costs down. For LED product wafers, yields must increase from their current levels to achieve industry-targeted cost levels. Yield loss in LEDs may arise in the forms of low output, decreased lifetime, shifted wavelength output and other properties. Many of the properties are not evaluated until LED product wafers are diced and sorted. With a long delay between LED wafer fabrication and LED property evaluation, correction of process drifts, excursion and other drivers of yield loss may not be corrected quickly enough leading to inefficiencies in wafer processing. For lighting applications LED output and color are important factors since the human eye may detect wavelength shifts as small as 1 nm at blue-green wavelengths and LEDs require color sorting for applications such as backlighting and general illumination to provide uniformity.

A main historical method for optical characterization of LEDs has been the use of photoluminescence which is the absorption and re-emission of photons by a material. Photoluminescence provides a rapid and non-contact method for determination of many parameters that affect yield. For LEDs of current market interest for lighting applications, especially Gallium Nitride ("GaN") and related alloys of Aluminum and Indium, UV light is used to excite photoluminescence of longer wavelengths of UV/Blue emission which is commonly phosphor converted to provide "white light."

FIG. 1 shows a pictorial schematic of a prior art workpiece characterization system 100. Workpiece characterization system 100 includes excitation source 110 which emits light 115 directed through optics 120, to be incident at angle $\Theta_1$ on workpiece 130. Photoluminescence emission light 140 derived from excitation of workpiece 130 is guided through optics 150 to light analyzing device 160 oriented at measurement angle $\Theta_2$. Excitation source 110 is commonly a narrow-band emission source such as a laser. Optics 120 and 150 may include any number of lenses, mirrors, filters or other optical elements necessary to transform light passing from excitation source 110 to workpiece 130 and/or from workpiece 130 to light analyzing device 160. Light analyzing device 160 is commonly a spectrograph, spectrometer, monochromator, photodiode, photomultiplier tube ("PMT") or other light analyzing device providing wavelength discrimination. By configuring workpiece characterization system 100 such that the incident and reflected angles, $\Theta_1$ and $\Theta_2$ respectively, are non-equal; saturation and or contamination of the photoluminescence emission light 140 by specularly scattered excitation light 117 is avoided.

The aforedescribed workpiece characterization system 100 presents multiple limitations which are discussed herein below. The present invention seeks to mitigate the shortcomings of the prior art and provide systems and methods for rapid analysis of LED product wafers inline or in-situ enabling improved yield.

BRIEF SUMMARY OF THE INVENTION

The present invention is directed to a system, method and software product for simultaneously producing exciting and illuminating sources across disparate wavelength bands that correlate to a photoluminescent device such as LEDs. Initially, the expected characteristics for a workpiece material may be estimated or referenced to a known calibration sample. These characteristics include the region of high absorption wavelengths for the material, the photoluminescence emission region for the material and a region of wavelengths with encoded information about the. A single broadband light source is provided that generates a wide spectrum of light that traverses each of the regions of high absorption, the photoluminescence emission region and the region of wavelengths with encoded information, but may not encompass each region or band. In so doing, a single light source can be used as an excitation source for exciting emissions from the workpiece and an illumination source for simultaneously reflecting the illumination light off the workpiece, each along a co-aligned path to and from a single measurement point on the workpiece.

One or more analyses methods can be provided for analyzing the emissions from the workpiece for such parameter characteristics as the amplitude, the mean wavelength value and full-width-half-maximum of the photoluminescence emissions. Additionally, the reflected illumination light from the workpiece can be separately analyzed for encoded information indicative of the thickness and optical properties of the layer(s) within the workpiece. Typically, the encoded light signal may be normalized to a known sample workpiece material prior to analysis.

Light wavelengths corresponding to, at least, the wavelengths of the photoluminescence emission region are filtered from the wide spectrum of light using a minus filter. Additionally or alternatively, the filtered band does not extend into wavelengths corresponding to the region of wavelengths with encoded information. In so doing, light generated by a single broadband light source can both excite emissions from the workpiece that can be measured and simultaneously illuminate the workpiece across the region of wavelengths useful for encoding information from the workpiece, the reflected light from which can also be analyzed. Furthermore, light reflected from workpiece originating from the single light source (either excitation or illumination light) will not conflict with the photoluminescence light emitted by the workpiece, thereby allowing for highly accurate measurements of the emitted photoluminescence light using the single broadband light source. The use of a single broadband light source as both the excitation source and the illumination source greatly simplifies directing the source light to a single measurement point on the workpiece as they follow a single co-aligned path to the measurement point for both the excitation source light and the illumination source light.

Workpiece materials that cannot be excited to emit light emissions at a useful level can be further excited by a supplemental excitation source, source as a laser. Alternatively, the laser excitation source can replace the broadband excitation source altogether. Optionally, the path of laser excitation source is co-aligned with the path of the illumination source and, if present, the path of broadband excitation source.

Additionally, the minus filter may filter a wide band of wavelengths from the excitation and illumination source light, wider or narrower than the photoluminescence emission region. For example, the filtered region may also include the band of leakage wavelengths, thereby eliminating spectral leakage wavelengths from the light source that might be reflected into the analysis system. Hence, spectral leakage is abated.

BRIEF DESCRIPTION OF THE SEVERAL VIEWS OF THE DRAWINGS

The novel features believed characteristic of the present invention are set forth in the appended claims. The invention itself, however, as well as a preferred mode of use, further objectives and advantages thereof, will be best understood by reference to the following detailed description of the illustrative embodiments when read in conjunction with the accompanying drawings wherein:

Figure 1:
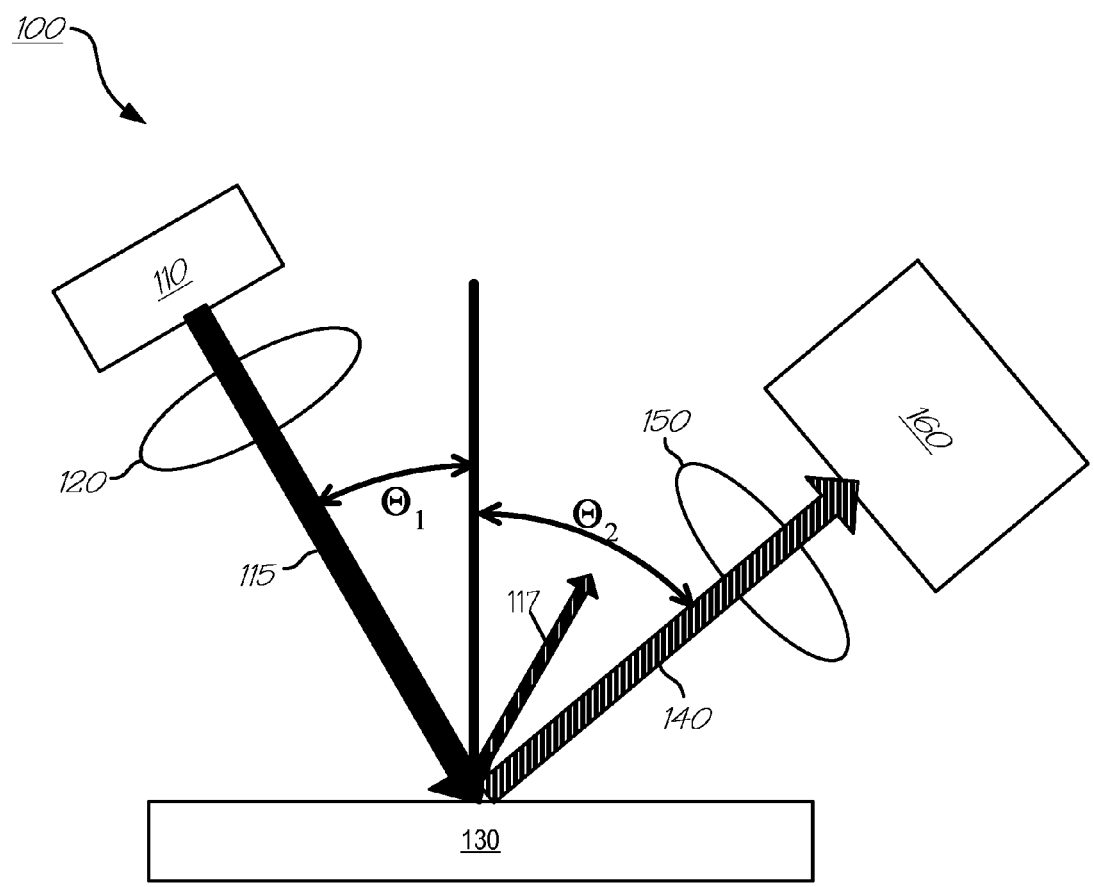
FIG. 1 is a pictorial schematic of a prior art workpiece characterization system.

Other features of the present invention will be apparent from the accompanying drawings and from the following detailed description.

DETAILED DESCRIPTION OF THE INVENTION

Element Reference Number Designations

100: Workpiece characterization system
110: Excitation source
115: Light
117: Specularly scattered excitation light
120: Optics
130: Workpiece
140: Photoluminescence emission light
150: Optics
160: Light analyzing device
200: Plot of the refractive index and extinction coefficient vs. wavelength for GaN
210: Extinction coefficient vs. wavelength
220: Refractive index vs. wavelength
300: Plot of the reflectance vs. wavelength for GaN
310: Reflectance vs. wavelength
400: Plot of the typical photoluminescence emission curve for GaN
410: Modulated photoluminescence emission vs. wavelength
415: Unmodulated photoluminescence emission vs. wavelength
420: High absorption wavelength region
425: 375 nm laser line
500: Plot of the de-modulated photoluminescence emission curve for GaN
510: Unmodulated photoluminescence emission vs. wavelength
515: Amplitude measurement
520: Mean wavelength measurement
525: Full-width-half-maximum
600: Plot of a spectral curve pulsed Xenon light vs. wavelength
610: Xenon light vs. wavelength
700: Plot of an exemplary spectrum spectral vs. wavelength
710: Exemplary spectrum vs. wavelength
800: Plots of actual and ideal spectral filter transmission curves vs. wavelength
810: Actual spectral filter transmission curve vs. wavelength
820: Ideal spectral filter transmission curve vs. wavelength
900: Plots of an exemplary scaled reflectance spectrum vs. wavelength
910: Scaled reflectance spectrum vs. wavelength
1000: Workpiece characterization system
1010: Non-continuous light source
1015: Source optical fiber assembly
1020: Spectrograph
1024: Signal optical fiber assembly
1030: Optical assembly
1035: Wavelength calibration element
1040: Workpiece interrogation/excitation light signal
1050: Workpiece
1060: Witness/reference sample
1105: Source point
1110: Lens 1120: Light filter(s)
1130: Dichroic mirror
1140: Lens
1145: Measurement point
1160: Lens
1165: Signal point
1170: Calibration lamp
1180: Photodiode
1210: Off-axis parabolic mirror
1220: Off-axis parabolic mirror
1300: Workpiece characterization system
1310: Laser
1312: Lens
1314: Lens
1316: Mirror
1320: Flashlamp
1330: Beamsplitter
1340: Lens
1350: Light filter
1360: Dichroic mirror
1370: Longpass light filter
1380: Dichroic mirror
1390: Focusing lens
1395: Lens
1397: Photoluminescence collection point
1399: Encoded light signal collection point In the following description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following description is, therefore, not to be taken in a limiting sense. For clarity of exposition, like features shown in the accompanying drawings are indicated with like reference numerals and similar features as shown in alternate embodiments in the drawings are indicated with similar reference numerals.

Prior art systems such as workpiece characterization system 100 limit the ability to perform multiple desired and/or required characterization measurements of workpieces and are often non-optimal and costly. Furthermore, the non-normally incident geometry of such prior art systems is inadequate or difficult for integration with and limits their functionality for in-situ and/or inline applications. To overcome the shortcomings of prior art systems, the present invention generally includes a system and method for workpiece characterization, which increases system performance, decreases system cost, enables multiple simultaneous measurement of workpiece characteristics and increases integrability/functionality. Other advantages of the current invention will be described below in association with described embodiments.

Figure 2:
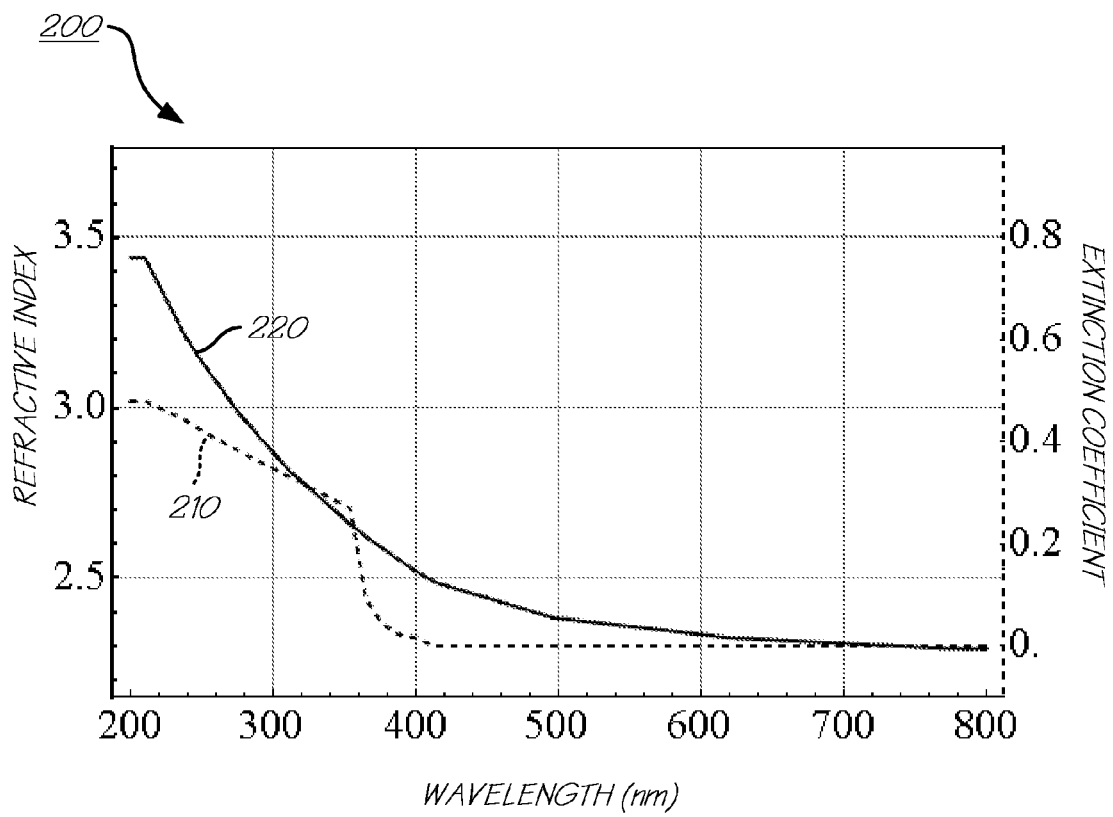
FIG. 2 is a plot of the optical indices of GaN, in accordance with an embodiment.

FIG. 2 shows plot 200 of the optical indices (commonly named "n" and "k", for the refractive index and extinction coefficient, respectively) of an exemplary sample of GaN. GaN and the ternary alloys of GaN with Aluminum and Indium see common use in the production of UV-emitting LEDS used for light applications upon phosphor conversion to white-light. For the purposes of describing the present invention, the discussions hereinafter will refer to LED devices comprised of an exemplary GaN material. However, the presently described invention is equally useful for other LEDs using other compositions.

For photoluminescence to occur, absorption of photons must occur in the material. As shown by dashed curve 210 of the extinction coefficient of GaN, absorption of light occurs increasingly at wavelengths less than 400 nm with a dramatic increase at approximately 360 nm. Commercial application of lasers for excitation of GaN materials are limited to a discrete number of wavelengths. A 405 nm wavelength laser is commonly available but does not provide significant photoluminescence emission due to the limited absorption. A 375 nm wavelength laser is also available although inhibited by very high cost and very short lifetimes of a few thousand hours. Furthermore, photoluminescence excitation using a 375 nm wavelength laser may be non-optimal due to the major absorption edge for GaN occurring at wavelengths slightly less than the 375 nm laser line. Tripled-YAG lasers at 355 nm wavelength and other lasers are also available but are again short-lived and/or prohibitively expensive. The absorption edge of the photoluminescent material may also move due to the alloy composition and/or temperature of the material during excitation.

Figure 3:
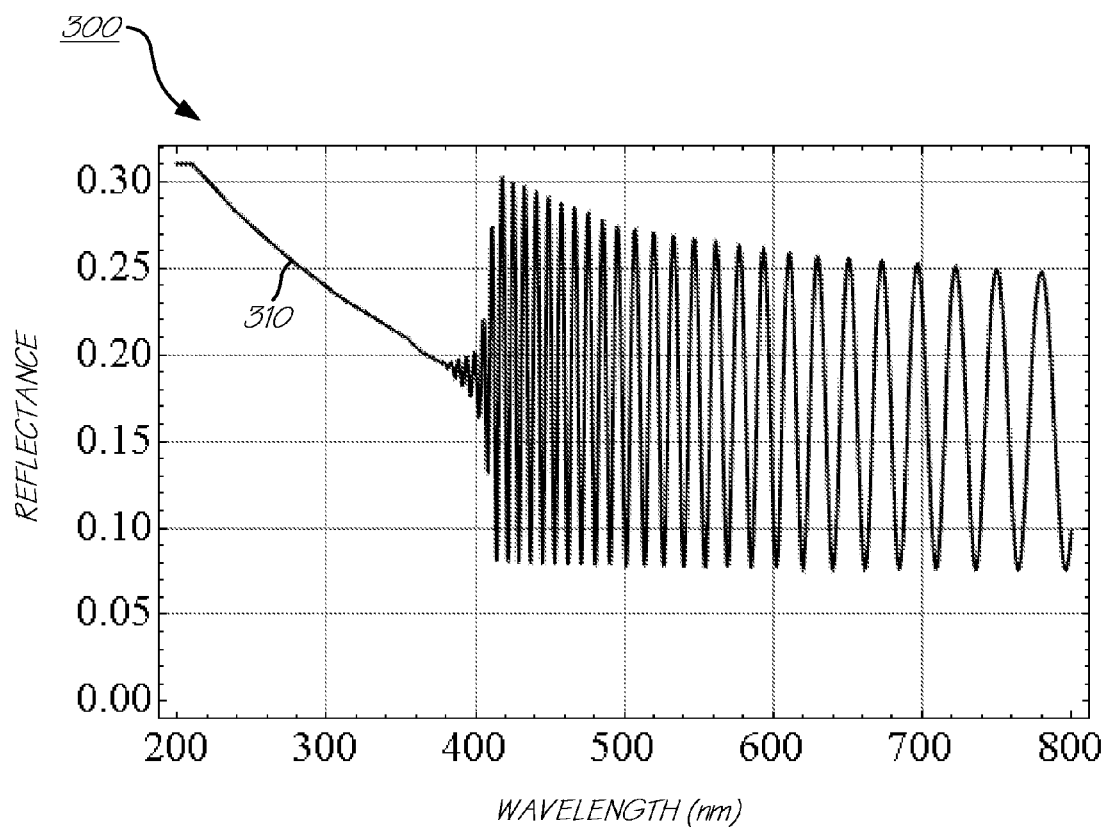
FIG. 3 is a plot of the reflectance of a 4 micron thick GaN film on a sapphire substrate showing the encoding of the optical properties of the structure, in accordance with an embodiment.

The refractive index of GaN is represented by solid curve 220. As may be seen from curve 220, the refractive index of GaN is less dependent upon wavelength for longer wavelengths. As described herein, it is advantageous to use the longer wavelengths of light for determination of thickness of GaN and its alloys since as discussed in U. Tisch et al; J. Appl. Phys., Vol. 89, No. 5, 1 Mar. 2001; "Dependence of the refractive index of AlxGa1-xN on temperature and composition at elevated temperatures" which is incorporated herein by reference, the optical indices of GaN and its alloys are functions of stoichiometry, temperature, crystallinity and other factors. The use of long wavelengths at least partially mitigates these effects and reduces variation in determined thicknesses. Relatedly, FIG. 3 shows plot 300 of reflectance curve 310 of a 4 micron thick GaN film on a sapphire substrate showing the encoding of the optical and thickness properties of the structure. The optical and thickness properties of the structure are encoded by the creation of interference fringes in the reflectance curve with spacings and amplitudes related to the refractive index, extinction coefficient and thickness of the material layers of the structure, as well as the angles of incidence and reflection of the light interrogating the structure.

Figure 4:
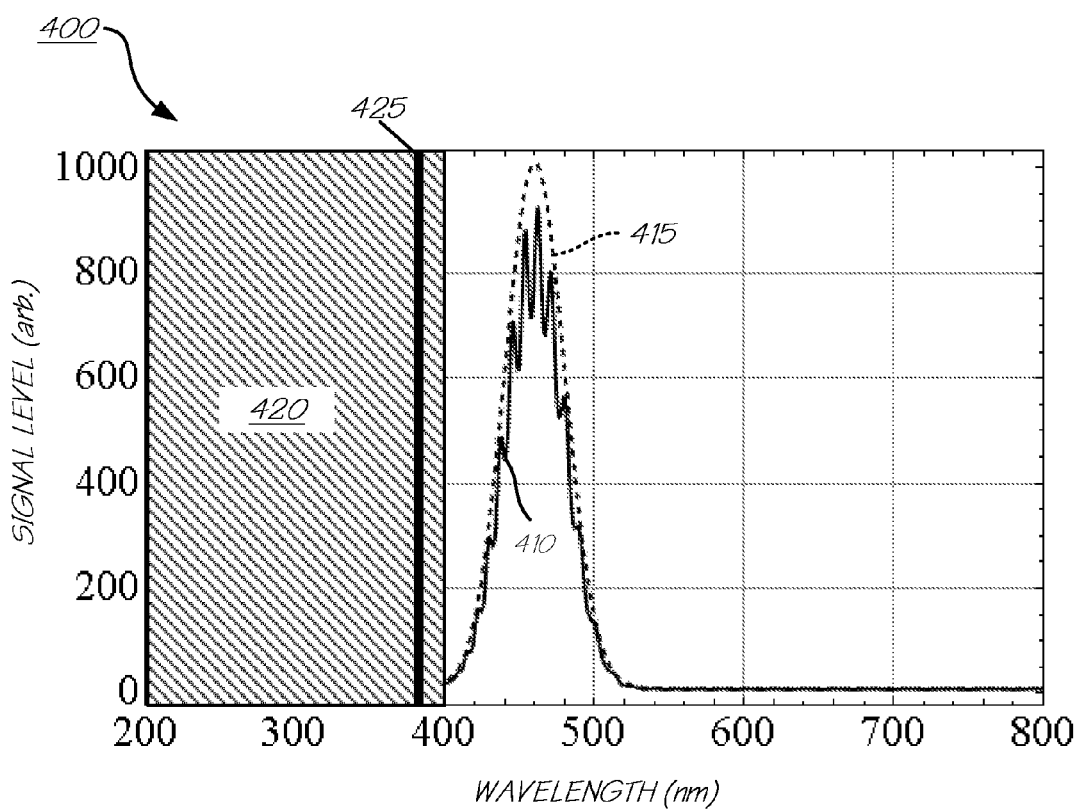
FIG. 4 is a plot of a typical photoluminescence emission curve for a GaN multiple quantum well ("MQW") LED and the wavelength region of high absorption of light for GaN.

FIG. 4 shows plot 400 of typical photoluminescence emission curve 410 for a GaN multiple quantum well ("MQW") LED. A photoluminescence emission curve may include modulation due to Fabry-Perot interference of the emission within the layered structure, such as shown by curve 410 or may not include modulation, such as indicated by dashed curve 415. One cause of such lack of modulation in a photoluminescence emission curve is due to the use of patterned sapphire substrates ("PSS") for construction of the LED structure. The patterning of the features on the sapphire substrate is specifically designed to reduce the modulation. Plot 400 also shows wavelength region 420 (indicated by a hashed region) of high absorption of light for GaN. As indicated by the extinction coefficient ("k") curve 210 of FIG. 2, photoluminescence emission may be excited by emission starting with wavelengths of light near 400 nm and extending to shorter wavelengths. Laser line 425 at 375 nm is also indicated. As discussed herein below, in association with FIG. 6, it is shown that a Xenon flashlamp source of the current invention provides useful light for excitation throughout the entire 200-400 nm wavelength region.

Figure 5:
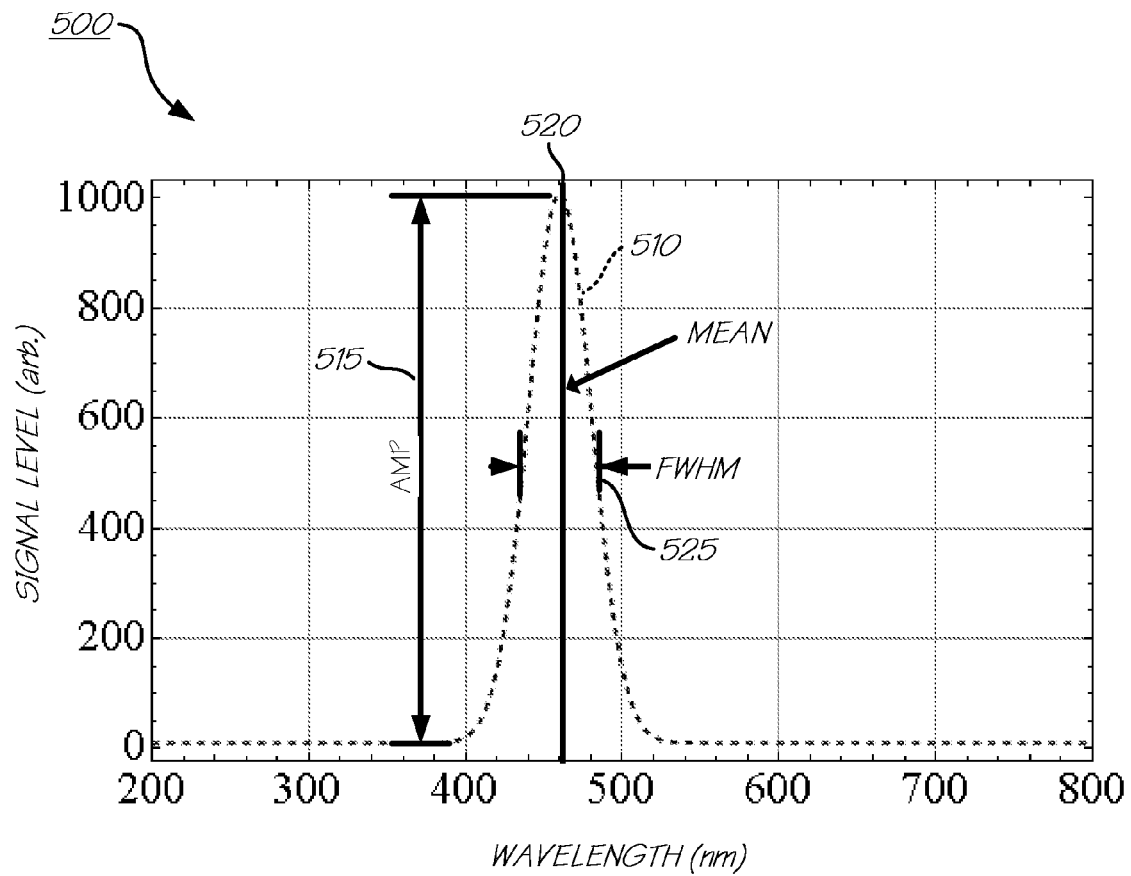
FIG. 5 is a plot of a representative photoluminescence emission curve and typical parameters of interest for yield/process control derivable from a photoluminescence emission curve.

FIG. 5 shows plot 500 of representative unmodulated photoluminescence emission curve 510 and typical parameters of interest derivable from photoluminescence emission curve 510. Photoluminescence emission curve 510 may originate from data collection as a modulated photoluminescence emission curve, such as curve 410 of FIG. 4 and require processing, such as Fourier filtering or model fitting to remove the modulation of the interference. Derivable parameters of interest include amplitude 515, mean wavelength value 520 and full-width-half-maximum ("FWHM") 525 of emission curve 510. These parameters may be determined by calculations, such as Gaussian and/or Voigt model fits, generalized linear or nonlinear peak fitting, pattern matching, moment calculations and other parameterization methods, such as partial least squares regression ("PLS") and principle component analysis ("PCA"). Determination of these parameters permit yield analysis, LED sorting and feedback/feedforward optimization of workpiece manufacturing processes.

Figure 6:
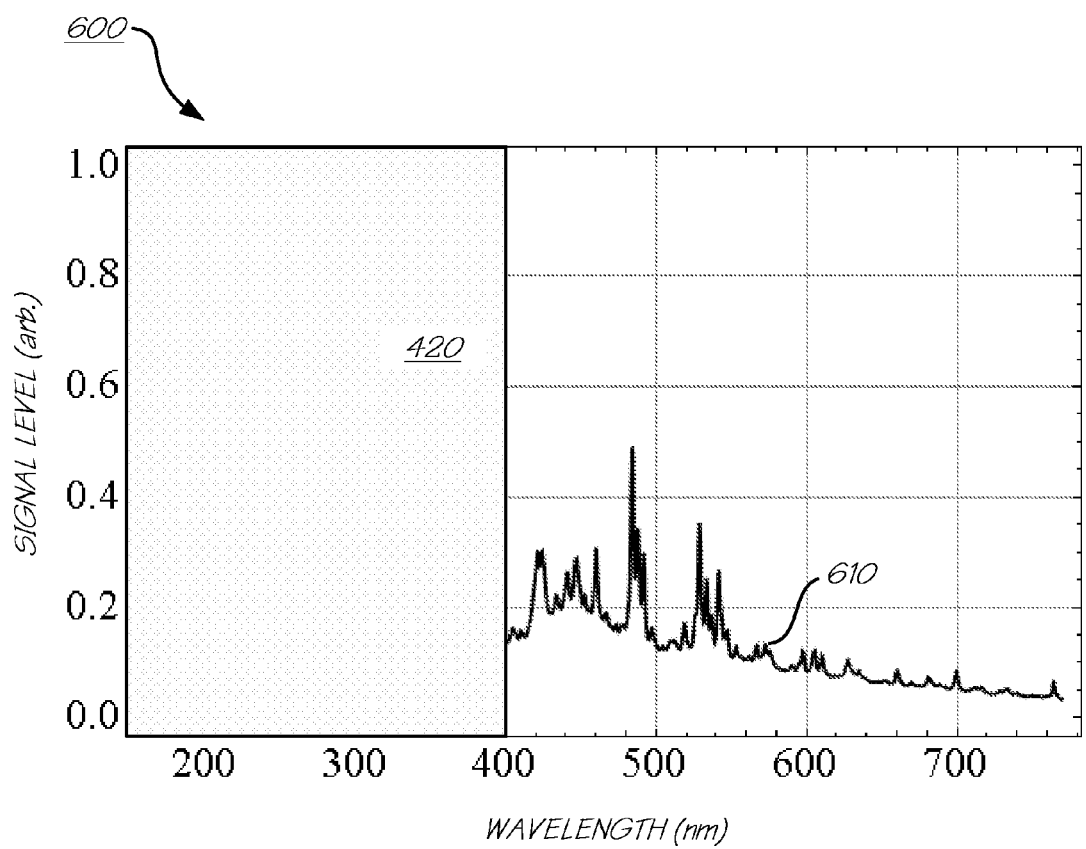
FIG. 6 is a plot of the spectral output of a pulsed Xenon flashlamp, in accordance with an exemplary embodiment of the present invention.

FIG. 6 shows plot 600 of spectral curve 610 of light emitted from a pulsed Xenon flashlamp with the wavelength region 420 (hashed region) of high absorption of light for GaN superimposed. For the purposes of describing the present invention, the discussions hereinafter will make reference a pulsed flashlamp-type light source. However, what is needed for practicing the present invention is a non-continuous light source for at least exciting an LED workpiece. The non-continuous light source need not necessarily be comprised of a pulsed flashlamp, but might instead be comprised of a shutterable continuous light source for providing a non-continuous light at the measurement point of an LED workpiece.

The flashlamp is able to excite GaN over an extensive wavelength band and is, therefore, less sensitive to the location and level of the absorption edge and functional wavelength dependence of the extinction coefficient(s) of the material layer(s). Optical output of Xenon flashlamps is inherently bright in UV. Estimated energy for a typical 20 Watt flashlamp (e.g., Excelitas FX1161 lamp) is approximately 20 µJ per flash for emissions between 200-400 nm. A flashlamp also provides a benefit in the ability to map moving workpieces without spatial blurring due to the approximately 1 µS duration of the pulse. Furthermore, a flashlamp provides the ability to collect measurements of photoluminescence and optical property information simultaneously with a single probe beam that inherently probes photoluminescence and thickness information at the same workpiece location, precisely.

A flashlamp is also able to excite an intensity witness sample, such as Nd:YAG, for integrated intensity referencing. Nd:YAG excitation is poor with commercial diode lasers at 375 nm since the optimal UV absorption of Nd:YAG occurs at approximately 355 nm. Flashlamp sources also provide extremely long lifetimes with on the order of 1E9 pulses whereby providing potentially years of service, depending on pulse rates in use. Comparatively, commercially available 375 nm laser diode sources have lifetimes of approximately 5000 hours. The broad spectral output from a flashlamp also supports interrogation and encoding of thickness information over a longer wavelength region with the same source used for photoluminescence excitation.

Figure 7:
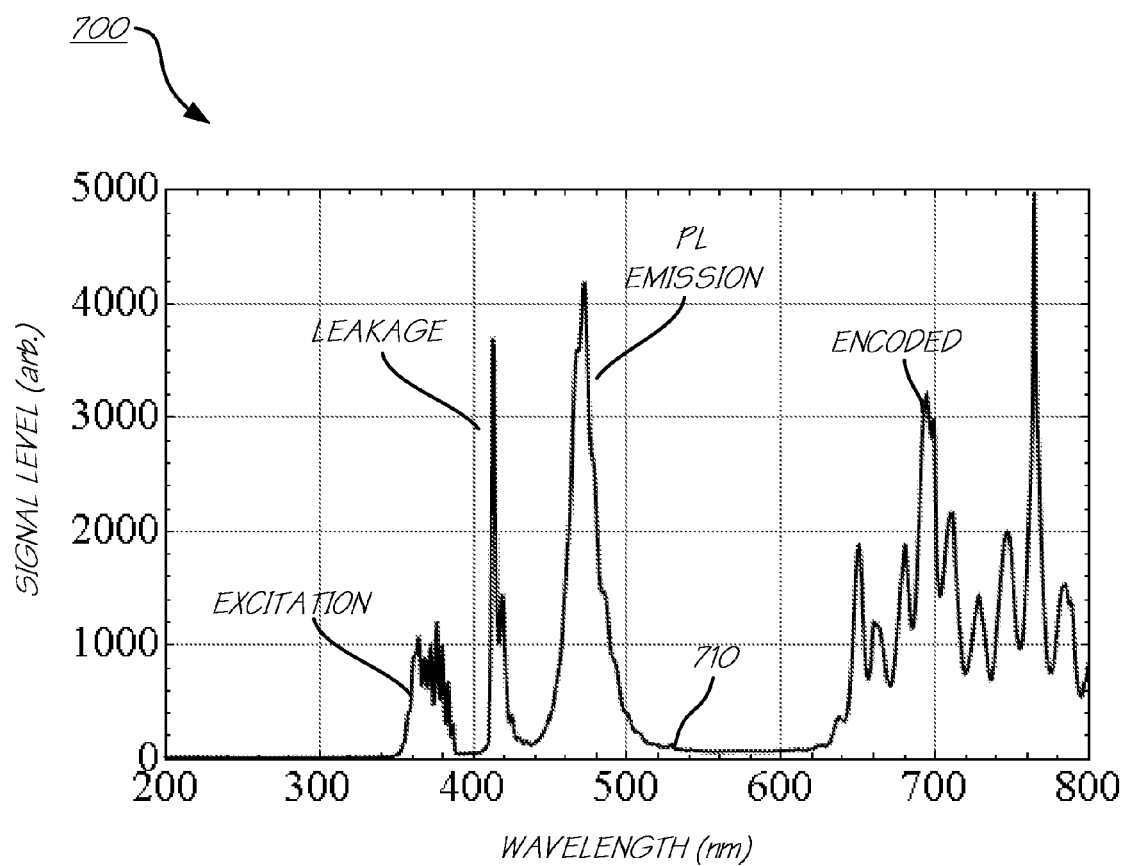
FIG. 7 is a plot of a representative spectrum of wavelength multiplexed information, collected in accordance with another exemplary embodiment of the present invention.

FIG. 7 shows plot 700 of representative spectrum 710, collected with an experimental embodiment of the current invention. Spectrum 710 includes multiple forms of information and features indicative of the interaction of the light sourced from a Xenon flashlamp, optical elements and a photoluminescent workpiece undergoing characterization. By carefully designed wavelength multiplexing, each type of information is available in defined wavelength regions, thereby reducing or eliminating confusion of information. Spectral features (labeled EXCITATION) of spectrum 710 at wavelengths from approximately 350-400 nm indicate a portion of the flashlamp excitation light directed to the workpiece and ultimately collected by a light analyzing device. Spectral features (labeled LEAKAGE) of spectrum 710 at wavelengths from approximately 410-440 nm indicate a portion of the flashlamp light, not useful for excitation or thickness encoding; although leaking through the optical assembly and ultimately collected by a light analyzing device. This spectral leakage is discussed herein to highlight the significance of spectral filtering to properly define the spectral regions for wavelength multiplexing. Spectral features (labeled PL EMISSION) of spectrum 710 at wavelengths from approximately 440-540 nm indicate photoluminescence emission from the workpiece undergoing excitation. Spectral features (labeled ENCODED) of spectrum 710 at wavelengths from approximately 620-800 nm indicate a portion of the flashlamp light directed to the workpiece, encoding optical property, structure and thickness information from the workpiece and ultimately collected by a light analyzing device.

As may be observed in FIG. 7, each spectral feature and its associated information is separate. This separation eases the analysis of each feature and its associated information, as any deconvolution or other processing to isolate different types of information is not required. Data represented by each feature may be individually analyzed for desired/required information. For example, the data represented by the EXCITATION feature may be analyzed to determine properties of the flashlamp excitation, such as shot-to-shot stability. Additionally, the data represented by the LEAKAGE feature may be analyzed to determine the performance and monitor any deterioration of spectral filtering. As discussed herein above with respect to FIGS. 4 and 5, the data represented by the photoluminescence EMISSION feature may be analyzed to determine parameters of interest for the workpiece being characterized. Furthermore, the data represented by the ENCODED feature may be analyzed to determine the thickness and optical properties of one or more layers of an interrogated structure.

Figure 8:
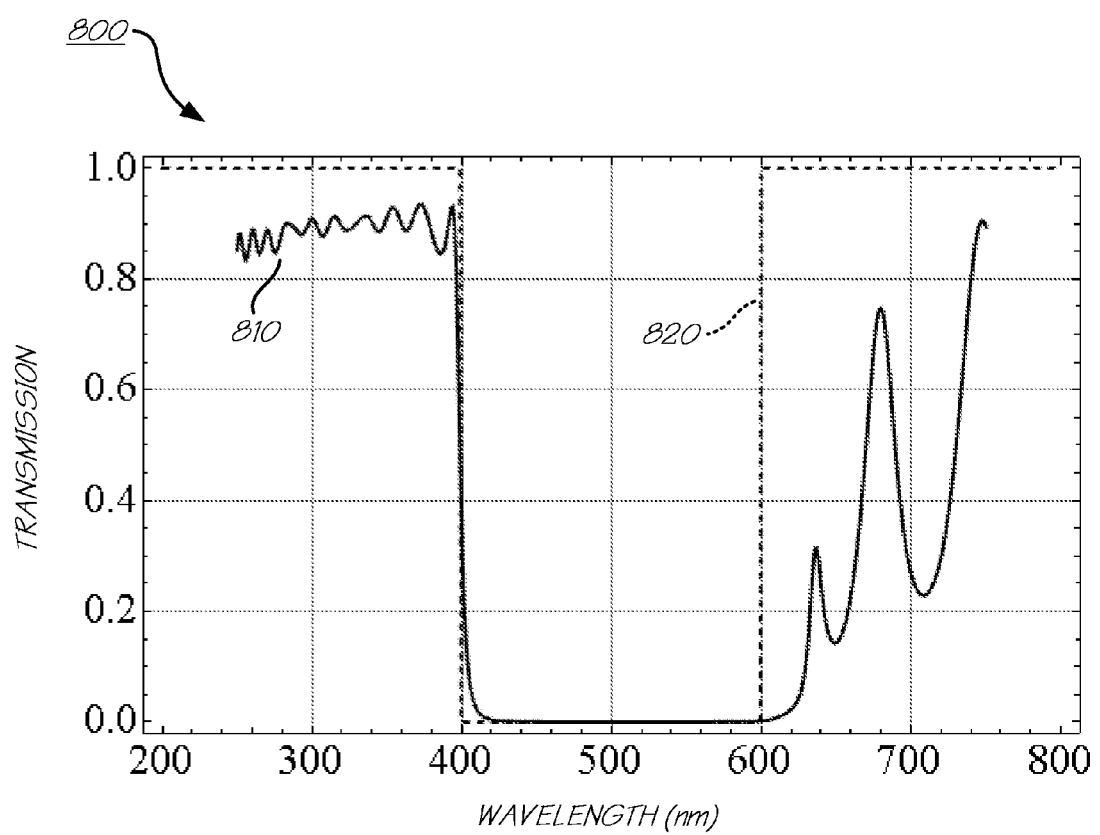
FIG. 8 is a plot of actual and ideal spectral filter transmission curves useful for filtering pulsed Xenon flashlamp output, in accordance with still another exemplary embodiment of the present invention.

FIG. 8 shows plot 800 of actual and ideal spectral filter transmission curves 810 and 820 respectively, useful for filtering pulsed Xenon flashlamp spectra to partition the spectra as discussed in association with FIG. 7 above. Actual and ideal spectral filter transmission curves 810 and 820, respectively, are exemplary for describing aspects of the present invention and not intended to limit the invention in any way. This type of filter is commonly referred to as a "minus" filter. Light filters of the type for generating represented by transmission curve 810 are extremely well known and understood in the relevant technological art and are readily available from commercial sources. The filter itself, may be created from one or more individual thin film filters, such as shortpass filters available from Edmund Optics of Barrington, N.J. A more specialized filter may be designed based upon the design principles and example noted in A. Thelen, Design of Optical Interference Coatings, Chapter 7 "Minus Filters", pg 152.

High transmission in the 200-400 nm region permits delivery of UV wavelengths of light to a workpiece for photoluminescence excitation. For best utilization of the spectral output of a flashlamp, the transmission of this region should be as high as possible given realistic filter design/material constraints. Very low transmission in the 400-600 nm region permits rejection of visible wavelengths of light from the flashlamp so that they do not mix with photoluminescence emissions of similar wavelengths. Proper isolation of photoluminescence emission and flashlamp output requires that transmission in this spectral region be at or below 1:1000. High transmission in the 600-800 nm region permits delivery of red and near infrared ("NIR") wavelengths of light to a workpiece for optical property and thickness encoding. For best utilization of the spectral output of a flashlamp, the transmission of this region should be as high as possible given realistic filter design/material constraints subject to a primary requirement that the UV transmission be weighted more heavily than 600-800 nm transmission in any filter design. Higher transmission for UV excitation light is important for high signal to noise information of photoluminescence EMISSION spectral data where high precision of determined parameters is desired. ENCODED spectral data often does not require the same level of signal to noise as the excited photoluminescence EMISSION.

Here it should be mentioned that the precise character of actual and ideal spectral filter transmission curves 810 and 820 should be dependent upon the characteristics of the workpiece LED to be evaluated. For instance, it is well known in the applicable technical art that LED-types with a photoluminescent mean wavelength (520) toward the ultraviolet end of the spectrum are extremely useful in exciting phosphor coatings applied to the LED. Hence, in some instances it may be necessary to adjust the mean and/or band of the minus filter depending on the type of LED to be evaluated.

With further regard to minus filtering a wideband light signal from a single light source, it should be appreciated that the use of a single light source for realizing both photoluminance and encoding measurement characteristics of a workpiece has the further advantage of un-complicating the alignment of optics of the system. Because the light sources used for both the photoluminescent and reflectance measurement originate from the same source, no special attention is necessary for converging separate source beams to a single measurement point on the workpiece.

Figure 9:
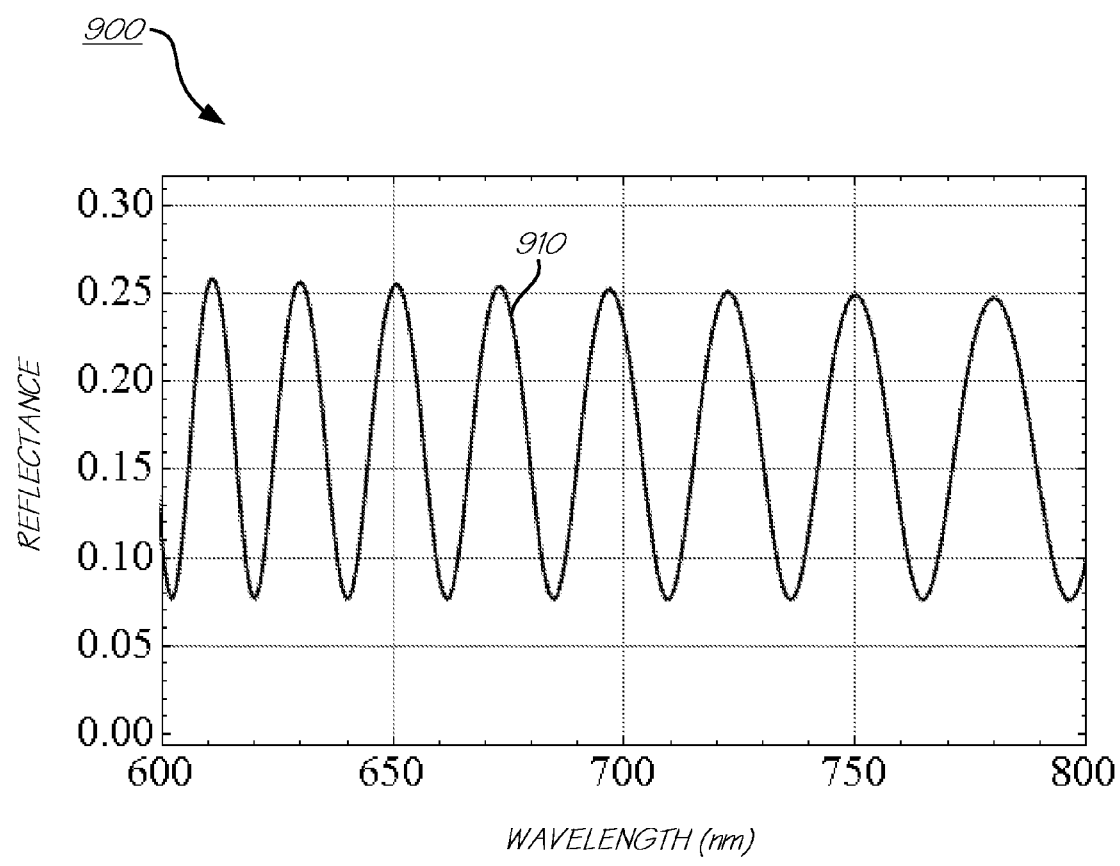
FIG. 9 is a plot of a portion of a scaled reflectance spectrum of a 4 micron thick GaN film showing the encoding of the optical and thickness properties of the layer.

FIG. 9 shows plot 900 of a portion of a scaled reflectance spectrum 910 of a 4 micron thick GaN film showing the thickness encoding of the optical properties of the layer. Due to the wavelength filtering of flashlamp emission as discussed above, light of wavelengths from approximately 600-800 nm is available for encoding of the thickness and optical properties of the layer(s). The use of wavelengths away from the photoluminescence emission wavelength region is beneficial for the reasons discussed above regarding temperature, stoichiometry and alloying. Additionally, these wavelengths are not as affected by the use of PSS substrates which suppress fringes specifically for the photoluminescence emission wavelength region and have less effect on the 600-800 nm wavelength region. An effect of using a PSS substrate may be 4× reduction of fringe contrast for thickness encoded spectra versus fringe contrast for lamellar substrates.

Spectrum 910 is scaled by taking uncorrected spectrum such as 710 of FIG. 7 and normalizing with respect to a known sample, commonly bare silicon (with or without native oxide). Spectrum 910 may also be processed by model fitting to determine a thickness of the "effective" thickness of the GaN layer(s) of the LED MQW. It may not be possible to determine the actual thicknesses of the multiple individual layers of a MQW structure, since each is very thin and potentially of graded refractive index.

Figure 10:
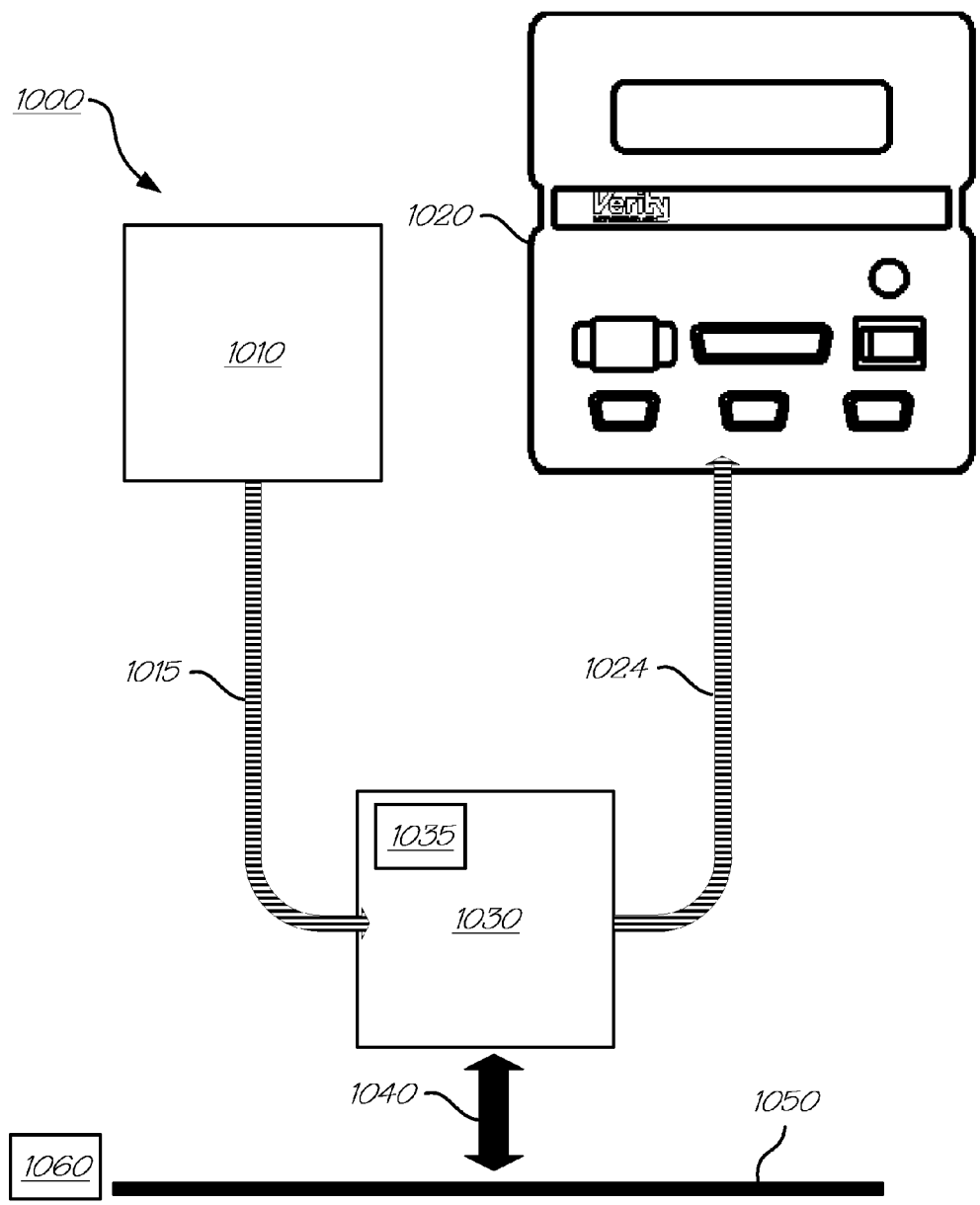
FIG. 10 is a pictorial schematic of the major elements of a workpiece characterization system, in accordance with an exemplary embodiment of the present invention.

FIG. 10 shows pictorial schematic of the major elements of exemplary workpiece characterization system 1000 of the present invention arranged to provide the benefits as detailed herein in accordance with one exemplary embodiment of the present invention. Workpiece characterization system 1000 includes non-continuous light source 1010, source optical fiber assembly 1015, spectrograph 1020, signal optical fiber assembly 1024, optical assembly 1030, workpiece illumination/excitation light signal 1040 and workpiece 1050. Non-continuous light source 1010 is connected via source optical fiber assembly 1015 with optical assembly 1030 to supply light signal 1040 to workpiece 1050. Spectrograph 1020 is connected via signal optical fiber assembly 1024 with optical assembly 1030 to receive a portion of workpiece interrogation light signal 1040 reflected and any excited photoluminescence emission light from workpiece 1050. Optical assembly 1030 directs illumination/excitation light 1040 to workpiece 1050 and collects photoluminescence and encoded illumination light reflected from workpiece 1050. Spectrograph 1020 may be a SD1024-series instrument from Verity Instruments of Carrollton, Tex. Non-continuous light source 1010 may be, for example, a compact flashlamp product such as the model 9456 available from Hamamatsu of Hamamatsu City, Japan or other flashlamp products available from Excelitas Technologies of Waltham, Mass. The use of alternate constructions of the optical assembly 1030 permit variation in lamp size and power, as well as allows physical constraints such as size, weight and/or thermal issues to be accommodated.

Optical assembly 1030 may include wavelength calibration element 1035 such as a neon lamp which emits spectral lines available for referencing. Witness/reference sample 1060 such as a Nd:YAG crystal, other photoluminescent material or silicon may be positioned at/on a surface coincident with the surface of an interrogated workpiece. As an intensity reference sample a bulk material such as a Nd:YAG crystal is preferred over a phosphor coated sample as it may be more stable.

Figure 11:
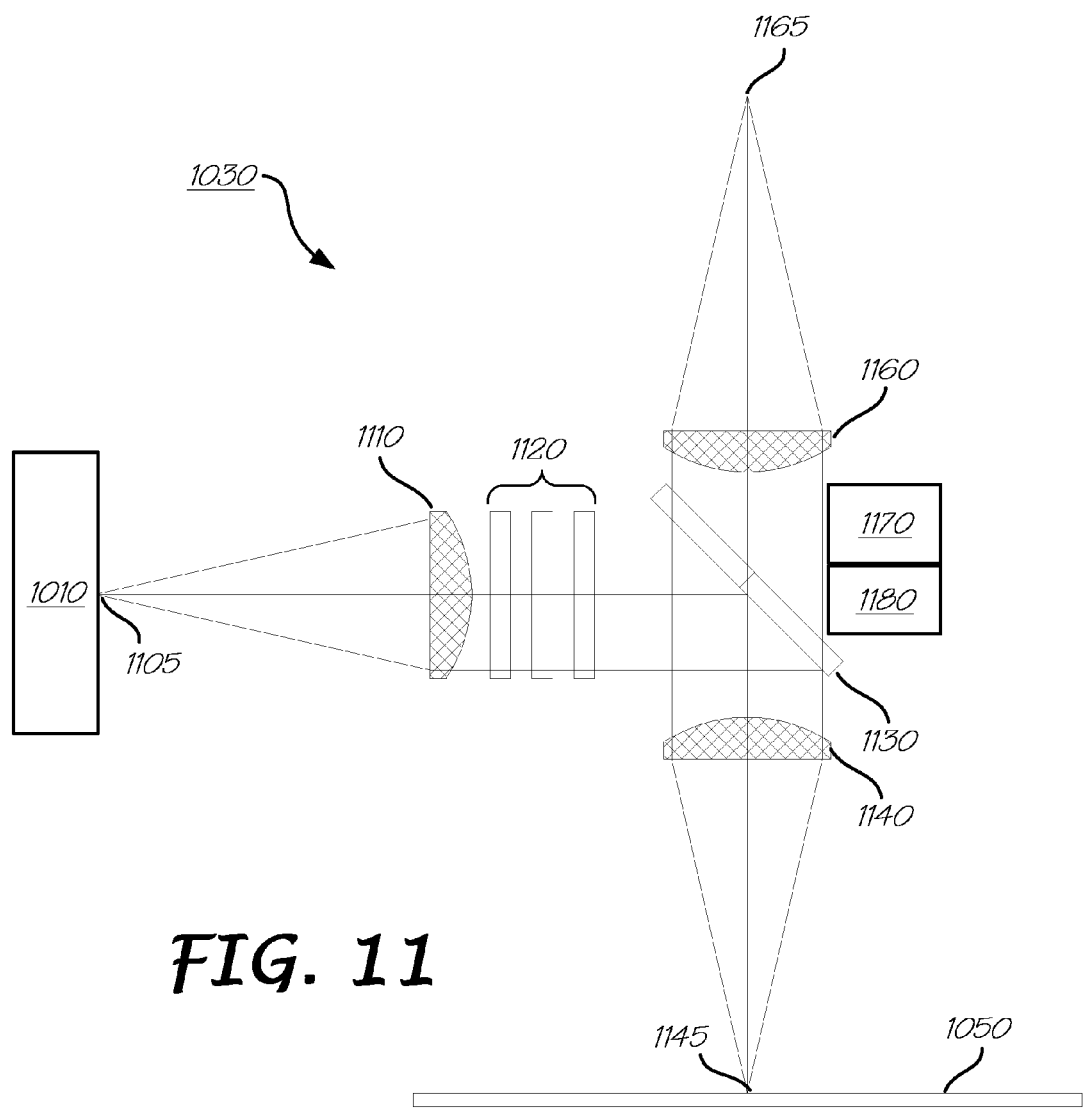
FIG. 11 is a diagrammatical cross-sectional view of the optical assembly of FIG. 10, showing additional details, in accordance with an exemplary embodiment of the present invention.

FIG. 11 shows a cross-sectional view of optical assembly 1030 of FIG. 10 in accordance with another exemplarily embodiment of the present invention. FIG. 10 illustrates additional details of optical assembly 1030. As depicted in the figure, in accordance with one exemplary embodiment of the present invention non-continuous light source 1010 may be directly coupled to optical assembly 1030 without intervening optical fiber assembly 1015, which may provide increased signal levels for excitation and illumination at the expense of a larger package size. Non-continuous light source 1010 simultaneously provides an excitation light for exciting workpiece 1050 and an illumination light for reflecting off workpiece 1050. Light originating from source point 1105 whether from optical fiber assembly 1015 or from non-continuous light source 1010 is collimated by lens 1110. Notice from the figure that all light originating from source point 1105 follows a single path to measurement point 1145, hence the path of the excitation light and illumination light are essentially co-aligned. Lens 1110 may be a silica lens or achromatic lens suitable for collimation of wavelengths from approximately 200-800 nm. Light collimated by lens 1110 is directed through filter(s) 1120, such as a filter defined by the transmissions curves of FIG. 8 to transform the spectrum emitted from non-continuous light source 1010 whereby removing an exemplary 400-600 nm photoluminescence emission band so as to avoid contamination of excited photoluminescence emission from a workpiece with wavelengths sourced by non-continuous light source 1010.

Collimated and filtered light is then directed to dichroic mirror 1130 which reflects light with wavelengths less than 400 nm and partially reflects/transmits wavelengths longer than 400 nm. For characterization of GaN devices, an ideal dichroic filter design for dichroic mirror 1130 has 100% reflection for wavelengths below 400 nm, 100% transmission for wavelengths in the band from 400-600 nm and 50% transmission for wavelengths greater than 600 nm. Collimated and filtered light is then directed by dichroic mirror 1130 to lens 1140. Lens 1140 may be a silica lens or achromatic lens suitable for collimation of wavelengths from approximately 200-800 nm. Collimated and filtered light is then directed through and focused by lens 1140 to workpiece 1050 (alternatively the light may be directed to witness or calibration sample during calibration and/or reference activity). The UV portion of the focused light excites photoluminescence emission from the workpiece and the resultant photoluminescence emission is collected and collimated by lens 1140. Simultaneously, the focused light with wavelengths greater than 600 nm is encoded by interaction with workpiece 1050 and is reflected from workpiece 1050 back through lens 1140 for collimation.

After collimation by lens 1140, both the photoluminescence emission and encoded light are directed to and are transmitted by dichroic mirror (which also acts as a filter) 1130 to lens 1160. Lens 1160 may be a silica lens or achromatic lens suitable for focusing wavelengths from approximately 400-800 nm. Upon transmission through lens 1160, light is focused by lens 1160 toward signal point 1165 where an optical fiber assembly (not shown) such as optical fiber assembly 1024 of FIG. 10 may be positioned to receive the focused light.

Optical assembly 1030 may also incorporate wavelength calibration lamp 1170 such as a NE-51 neon lamp and/or other subsystems such as photodiode 1180 or other sensor for monitoring consistency of the source emission for corrections due to mechanical, thermal aging or other sources of variation.

Figure 12:
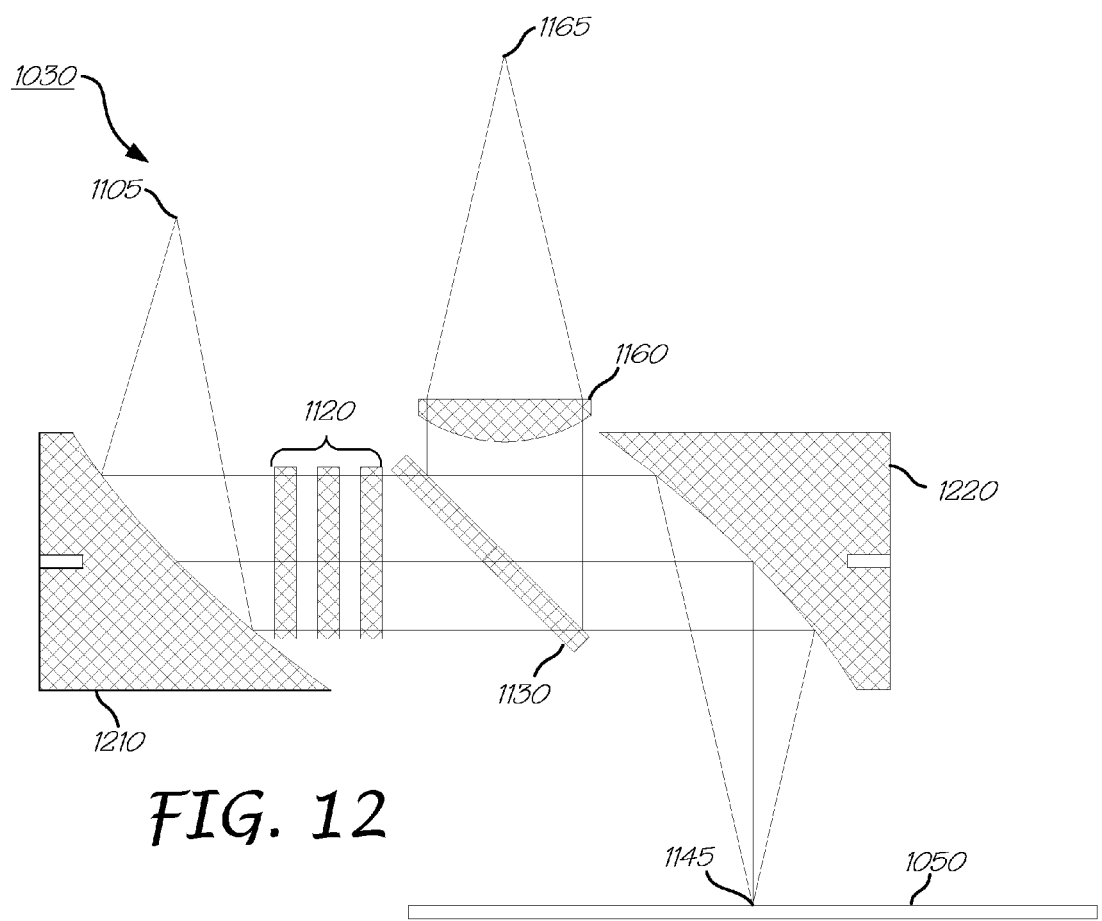
FIG. 12 is a diagrammatical cross-sectional view of an alternative construction of the optical assembly of FIG. 10, showing additional details, in accordance with an exemplary embodiment of the present invention.

FIG. 12 shows a cross-sectional view of an alternative construction of optical assembly 1030 of FIG. 10 in accordance with another exemplary embodiment of the present invention. Essentially, the construction of optical assembly 1030 of FIG. 11 differs from that depicted in FIG. 12 in that lenses 1110 and 1140 have been replaced with off-axis parabolic mirrors 1210 and 1220. Off-axis parabolic mirrors are well known and widely available from commercial vendors such as available from Newport Corporation of Irvine, Calif., which may improve imaging of the optical system and avoid the chromatic aberration caused by the use of lenses. All other optical elements of the optical assembly of FIG. 12 may remain as described in association with FIG. 11.

Figure 13:
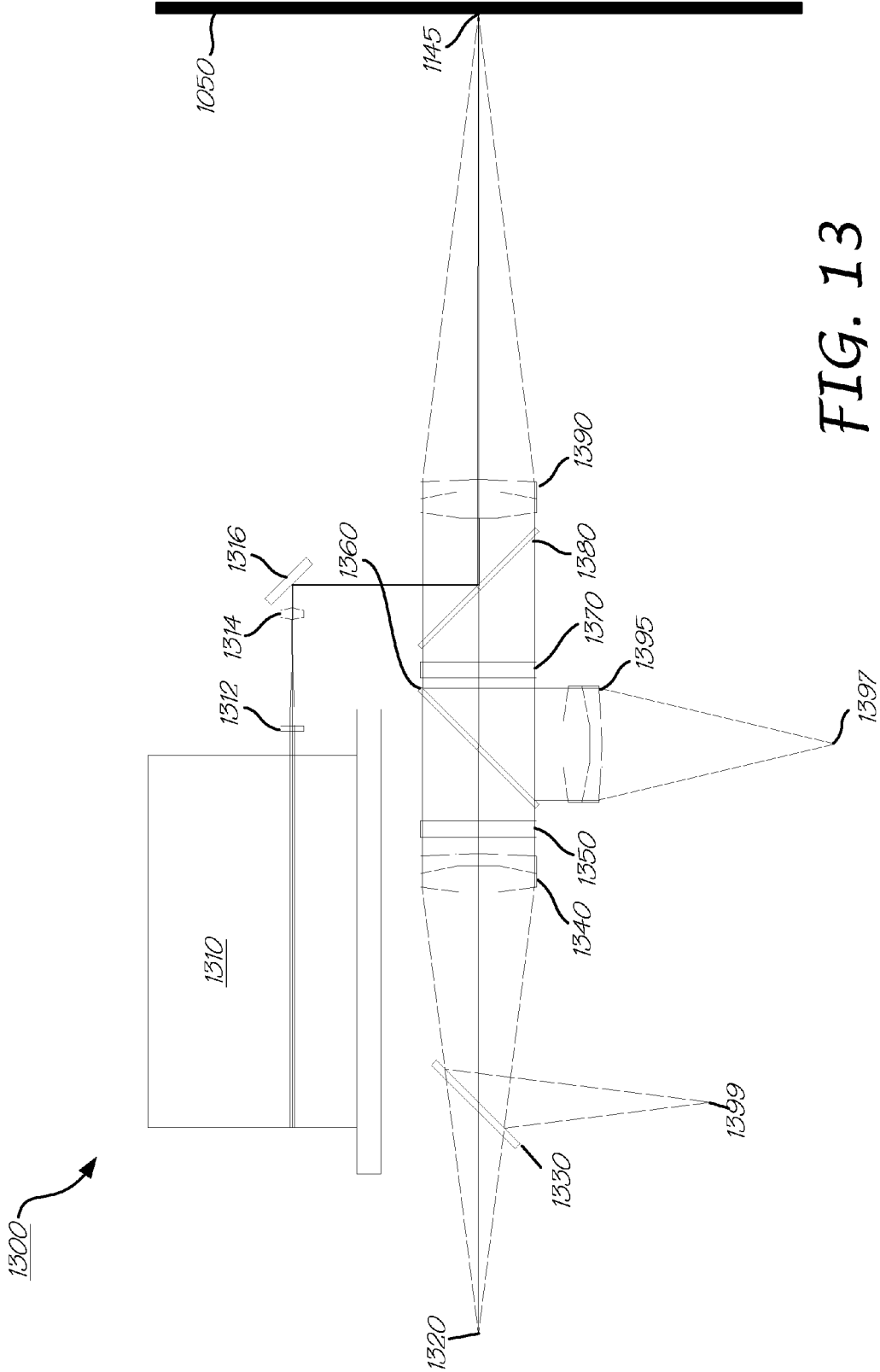
FIG. 13 is a diagrammatical cross-sectional view of another alternative construction of the optical assembly of FIG. 10, showing additional details, in accordance with an exemplary embodiment of the present invention.

FIG. 13 shows a cross-sectional view of another alternative construction of optical assembly 1030 of FIG. 10 in accordance with still another exemplary embodiment of the present invention. This embodiment of optical assembly 1030 illustrates further details potentially necessitated by workpieces having weak photoluminescence emission and/or reflectance characteristics. To accommodate weak signals, optical assembly 1300 includes laser source 1310 and additional optical elements to enhance both photoluminescence emission and flashlamp signals transmitted to and reflected from workpiece 1050. Flashlamp light may be sourced at point 1320 either directly or via optical fiber and is subsequently directed to beamsplitter 1330. The light is then transmitted through beamsplitter 1330 to lens 1340 where upon transmission through lens 1340 is collimated. Lens 1340 may be a silica lens or achromatic lens suitable for collimating/focusing wavelengths from approximately 600-800 nm.

Collimated light is then directed through filter 1350 to remove all wavelengths less than 600 nm. Filter 1350 is a normal incidence 600 nm longpass filter and may be located as shown in FIG. 13 or may be positioned between source point 1320 and beamsplitter 1330. Filter 1350 acts to isolate light of photoluminescence emission wavelengths from light in the 600-800 nm band. The longpass filtered light is transmitted through dichroic mirror 1360 through filter 1370, through dichroic mirror 1380 to focusing lens 1390 and ultimately to workpiece 1050. Dichroic mirror 1360 is a 600 nm longpass filter passing light of wavelengths greater than 600 nm but reflecting light of shorter wavelengths and acts to isolate light of photoluminescence emission wavelengths from light in the 600-800 nm band. Filter 1370 is a normal incidence 400 nm longpass filter and acts to isolate light of photoluminescence emission wavelengths and light in the 600-800 nm band from shorter wavelength excitation light.

Dichroic mirror 1380 is a 400 nm longpass filter passing light of wavelengths greater than 400 nm but reflecting light of shorter wavelengths and acts as beam combiner to integrate the laser into the optical path of the system as well as to isolate light of photoluminescence emission wavelengths and longer from light of less than 400 nm wavelength. Lens 1390 may be a silica lens or achromatic lens suitable for collimating/focusing wavelengths from approximately 400-800 nm and is selected to provide proper positioning of the laser beam waist and the focus of the 600-800 nm light from the flashlamp at measurement point 1145.

Light emitted from laser 1310 is transformed by lenses 1312 and 1314 for beam diameter and/or aspect ratio and may be redirected by mirror 1316 to dichroic mirror 1380 for combining into the optical path of optical assembly 1300. Upon reflection from dichroic mirror 1380 the laser light is directed to lens 1390 for focusing to workpiece 1050 at point 1145 whereby exciting photoluminescence emission of workpiece 1050. Photoluminescence emission light emitted from workpiece 1050 is collimated by lens 1390 and transmitted through dichroic mirror 1380 and filter 1370, is reflected from dichroic mirror 1360 to lens 1395 for focusing to point 1397 for collection via an optical fiber assembly, such as optical fiber assembly 1024 of FIG. 10 and delivery to a light analyzing device, such as light analyzing device 1020 of FIG. 10.

Encoded light reflected from workpiece 1050 is collimated by lens 1390 and transmitted through dichroic mirror 1380, filter 1370, dichroic mirror 1360 and filter 1350 to lens 1340 for focusing. Subsequent to transmission through lens 1340 encoded light is reflected from beamsplitter 1330 to point 1399 for collection via an optical fiber assembly and delivery to a light analyzing device. Since the light signals arriving at collection points 1397 and 1399 are spectrally unique, it is possible to simultaneously collect the photoluminescence emission and encoded light signals as shown in plot 700 of FIG. 7.

Figure 14:
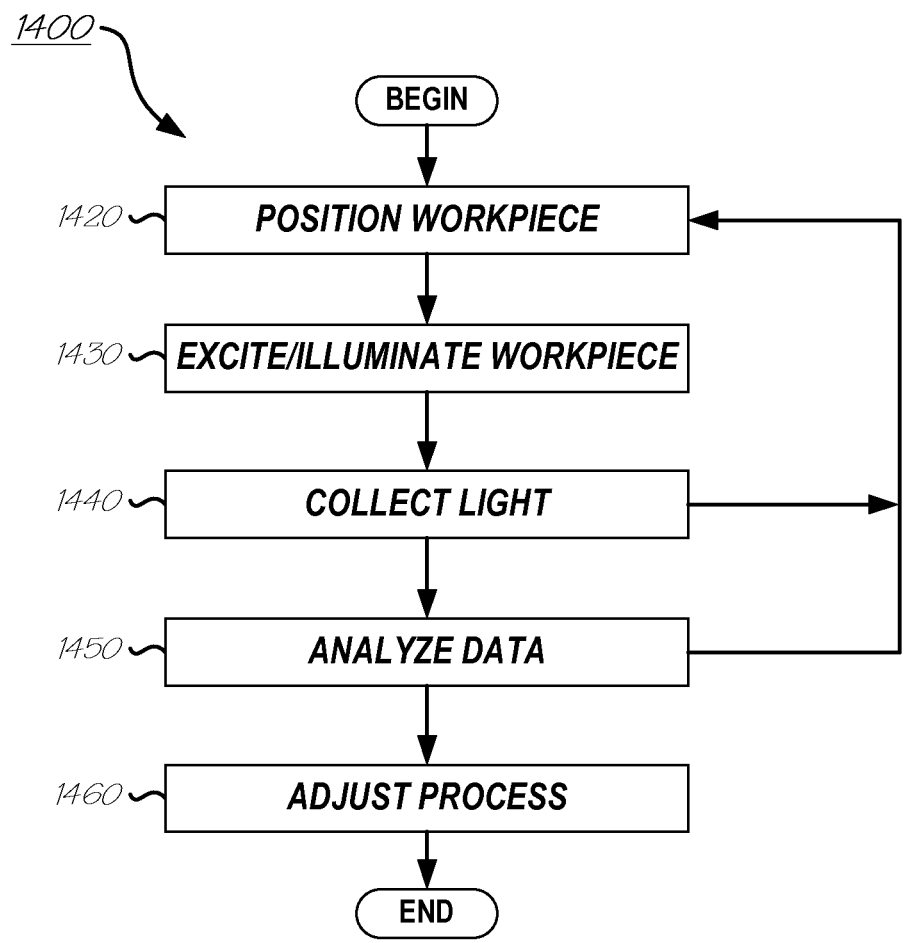
FIG. 14 is a flow chart of a process for operating a workpiece characterization system, in accordance with an exemplary embodiment of the present invention.

FIG. 14 shows a flow chart of process 1400 for operating a workpiece characterization system. Process 1400 begins with preparation step (not shown) wherein any necessary or desired setup or configuration of a characterization system is performed. Additionally or optionally reference materials and/or measurements/calibrations as discussed herein may be prepared during preparation. Process 1400 next advances to step 1420 wherein a workpiece may be positioned for measurement. Next in step 1430 a workpiece may be illuminated/excited by light sourced from a flashlamp and/or other light source. Upon satisfactorily performing the abovementioned steps, process 1400 advances to step 1440 wherein light is collected from a workpiece. At this step in process 1400 the process may return to step 1420 and reposition a workpiece for bulk data collection without immediate analysis or may advance to step 1450 wherein data derived from light collected by a light analyzing device is performed. Also at this step in process 1400 the process may return to step 1420 to reposition a workpiece. Following analysis of any/all available data, process 1400 advances to step 1460 wherein data analyzed during step 1450 may be used to adjust a workpiece manufacturing process in a feedback or feedforward manner such as by altering a layer deposition thickness or processing temperature for LED wafer manufacture. Process 1400 may be performed on workpieces either in-situ, inline, or external with processing of the workpieces. Process 1400 terminates with step 1470 wherein activities such as storing of data, validation of process changes, etc. may be performed. The collection and analysis of data from multiple locations on a workpiece may provide workpiece maps useful for sorting product prior to dicing, packaging, and probing.

It should be noted that the process for measurement of a reference or calibration sample is the same as for a workpiece as defined by process 1400. For collection of reference/calibration data a sample of known optical properties is placed in the location of the workpiece to be measured so as to reflect incident light, encoded with known properties of the calibration sample, back toward the measurement system as would a workpiece undergoing measurement. For example, a specularly reflective sample, such as a silicon workpiece, may be used and positioned in the workpiece operating position.

The changes described above, and others, may be made in the workpiece characterization systems described herein without departing from the scope hereof. For example, although certain examples are described in association with LED wafer processing equipment, it may be understood that the wafer characterization systems described herein may be adapted to other types of processing equipment such wafer implant monitoring, solar cell fabrication or any application where photoluminescence emission and thickness measurement may be required. Furthermore, although certain embodiments discussed herein describe the specific arrangement of optical elements, such as filters, lenses and beamsplitters, it should be understood that different arrangements may be used and may be functionally equivalent.

It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

The exemplary embodiments described below were selected and described in order to best explain the principles of the invention and the practical application, and to enable others of ordinary skill in the art to understand the invention for various embodiments with various modifications as are suited to the particular use contemplated. The particular embodiments described below are in no way intended to limit the scope of the present invention as it may be practiced in a variety of variations and environments without departing from the scope and intent of the invention. Thus, the present invention is not intended to be limited to the embodiment shown, but is to be accorded the widest scope consistent with the principles and features described herein.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

What is claimed is:

1. An optical characterization system for evaluating photoluminescence and property characteristics of a workpiece, said workpiece having workpiece material characteristics comprising an excitation region of high absorption wavelengths between a first wavelength and a second wavelength and photoluminescence emission region between a third wavelength and a fourth wavelength, wherein the said second wavelength is longer than said first wavelength, said third and fourth wavelength are longer than said first and second wavelengths and said fourth wavelength is longer than said third wavelength, the optical characterization system comprising:
    a broadband excitation light source for generating an excitation light across an excitation source region of wavelengths between a fifth wavelength and a sixth wavelength for exciting the workpiece material, wherein said second wavelength is longer than said fifth wavelength and said sixth wavelength is longer than said fourth wavelength, wherein the excitation source region of wavelengths encompasses the photoluminescence emission region of the workpiece material;
    a light filter optically coupled to said broadband excitation light source for spectral filtering a band of wavelengths of the excitation light encompassing the photoluminescence emission region of the excitation source region of wavelengths between a seventh wavelength and an eighth wavelength, wherein said seventh wavelength is longer than said second wavelength and shorter than said third wavelength, and said eighth wavelength is longer than said fourth wavelength;
    a light analyzer;
    first optical components optically coupled between the broadband excitation light source and the light analyzer for receiving the filtered excitation light and directing the filtered light to a measurement point on the workpiece; and
    second optical components optically coupled between the broadband excitation light source and the light analyzer for receiving light from the measurement point on the workpiece and directing the light from the measurement point on the workpiece to the light analyzer.

2. The optical characterization system of claim 1, wherein the light from the measurement point on the workpiece comprises photoluminescence emission emitted from the workpiece within the photoluminescence emission region between the third wavelength and the fourth wavelength.

3. The optical characterization system of claim 2, wherein the broadband excitation light source further comprises an illumination light source for illuminating an illumination region of wavelengths between a ninth wavelength and a tenth wavelength, within said ninth and tenth wavelengths are within said fifth and sixth wavelengths of the excitation light and said illumination region of wavelengths being longer than the eighth wavelength of the band of wavelengths filtered by the light filter, wherein the light from the measurement point on the workpiece further comprises reflected light within the ninth and tenth wavelengths of the illumination region, wherein the reflected light comprises encoded information relating to a property of the workpiece material.

4. The optical characterization system of claim 3, wherein the broadband excitation light source and the illumination light source comprise a single broadband light source.

5. The optical characterization system of claim 4, wherein the property of the workpiece material comprises one of a thickness of the material, a thickness of a layer within the material, thicknesses of a plurality of layers within the material, an index of refraction of the material, an extinction coefficient of the material, an index of refraction of a layers within the material, an extinction coefficient of a layers within the material, an index of refraction of a plurality of layers within the material and an extinction coefficient of a plurality of layers within the material.

6. The optical characterization system of claim 5, wherein the first optical components for receiving the filtered excitation light and directing the filtered light to the measurement point on the workpiece direct the filtered excitation light normally incident to the workpiece at said measurement point.

7. The optical characterization system of claim 6, wherein the second optical components for receiving light from the measurement point on the workpiece and directing the light from the measurement point on the workpiece to the light analyzer receive the light normally incident to the workpiece from the measurement point.

8. The optical characterization system of claim 1, wherein said broadband excitation light source further comprises a flashlamp.

9. The optical characterization system of claim 1, wherein said broadband excitation light source further comprises one of a non-continuous light source and a continuous light source.

10. The optical characterization system of claim 1, wherein said broadband excitation light source further comprises:
   a continuous light source; and
   a light shuttering mechanism for intermittently blocking the excitation light generated by the continuous light source.

11. The optical characterization system of claim 3, further comprises:
   a laser excitation source for generating a laser excitation light at one or more discrete excitation wavelengths within the high absorption wavelength region of the workpiece material; and
   third optical components for receiving the laser excitation light and directing the laser excitation light to the measurement point on the workpiece.

12. The optical characterization system of claim 4 wherein said single broadband light source and said laser excitation source comprise at least one of a laser, a flashlamp, an LED, a continuous source, a SLED and a tungsten-halogen source.

13. The optical characterization system of claim 1, wherein the third wavelength of the photoluminescence emission region is longer than 400 nm and the fourth wavelength of the photoluminescence emission region is shorter than 600 nm, and the spectral filtered band of wavelengths further comprises the seventh wavelength comprising a frequency of 400 nm and the eighth wavelength comprising a frequency of 600 nm.

14. The optical characterization system of claim 3, further comprising:
   a reference sample workpiece for referencing information derived from the photoluminescence emission region of the photoluminescence emissions emitted from the workpiece and from reflected light region reflected from the workpiece.

15. The optical characterization system of claim 3, wherein the first optical components for receiving the filtered excitation light and directing the filtered light to a measurement point on the workpiece further comprise one of a dichroic mirror and an off-axis parabolic mirror; and
   the second optical components for receiving light from the measurement point on the workpiece and directing the light from the measurement point on the workpiece to the light analyzer further comprise one of a dichroic mirror and an off-axis parabolic mirror.

16. A method for simultaneous measurement of layer and photoluminescence properties of a workpiece comprising:
   impinging a spectrally filtered excitation source and a spectrally filtered illumination source upon a surface of said workpiece which responds to said excitation source by emitting photoluminescent light and said illumination source by encoding light from said illumination source with layer information, co-directing said photoluminescent light and said encoded light through an optical assembly whereby each light is directed to a common light analyzing device for measurement.

17. The method of claim 16, wherein said spectrally filtered excitation source and said spectrally filtered illumination source being generated at a single broadband light source.

18. The method of claim 16, wherein the measurement is performed during semiconductor processing and further comprising:
   moving said workpiece relative to said system whereby measuring multiple locations of said workpiece.

19. The method of claim 16, further comprising:
   measuring a reference sample;
   deriving information from said measuring; and
   using said information to reference information derived from said workpiece.

20. The method of claim 16, further comprising analyzing a measurement from said system to derive parameters indicative of the state of the workpiece.

* * * * *